United States Patent [19]
Hoff et al.

[11] Patent Number: 5,543,026
[45] Date of Patent: Aug. 6, 1996

[54] REAL-TIME SCANNING FLUORESCENCE ELECTROPHORESIS APPARATUS FOR THE ANALYSIS OF POLYNUCLEOTIDE FRAGMENTS

[75] Inventors: Louis B. Hoff, Belmont; Eric W. Lachenmeier, La Honda; Yefim M. Raysberg, Fremont; Eric S. Nordman, Palo Alto, all of Calif.

[73] Assignee: The Perkin-Elmer Corporation, Foster City, Calif.

[21] Appl. No.: 192,485

[22] Filed: Feb. 7, 1994

[51] Int. Cl.$^6$ .............................. C02F 1/40; C02F 11/00; C25B 9/00; C25B 11/00
[52] U.S. Cl. ....................... 204/612; 204/616; 204/621
[58] Field of Search .......................... 204/299 R, 180.1, 204/182.8

[56] References Cited

U.S. PATENT DOCUMENTS

| | | |
|---|---|---|
| 4,683,202 | 10/1985 | Mullis . |
| 4,811,218 | 6/1986 | Hunkapiller ................. 364/413.01 |
| 4,957,613 | 9/1990 | Schuette ........................ 204/182.8 |
| 4,975,170 | 12/1990 | Hellman ....................... 204/299 R |
| 5,162,654 | 2/1991 | Kostichka et al. . |
| 5,192,412 | 3/1993 | Kambara et al. .............. 204/182.8 |

FOREIGN PATENT DOCUMENTS

| | | |
|---|---|---|
| 0314045 | 3/1989 | European Pat. Off. . . |
| 0339974 | 11/1989 | European Pat. Off. . . |
| 63-231247 | 9/1988 | Japan . |

OTHER PUBLICATIONS

Trainor Anal.Chem., 62: 418–426 (1990). DNA Sequencing, Automation and the Human Genome. Mar. 1, 1990.

Watkins BioTechniques, 6: 310–319 (1988). no month. Restricton Fragment Length Polymorphism (RFLP): Applications in Human Chromosome Mapping and Genetic Disease Research.

Ziegle et al. Genomics, 14: 1026–1031 (1992). no month. Application of Automated DNA Sizing Technology for Genotyping Microsatellite Loci.

Brumley et al. Nucleic Acids Research, 19: 4121–4126 (1991). no month. Rapid DNA Sequencing by Horizontal Ultrathin Gel Electrophoresis.

Stegemann et al. Methods in Molecular and Cellular Biology, 2: 182–184 (1991). no month. Automated DNA Sequencing on Ultrathin Slab Gels.

Karger et al. Nucleic Acids Research, 19: 4955–4962 (1991). no month. Multiwavelength Fluorescence Detection for DNA Sequencing Using Capillary Electrophoresis.

*Primary Examiner*—John Niebling
*Assistant Examiner*—Edna Wong
*Attorney, Agent, or Firm*—Paul D. Grossman

[57] ABSTRACT

This invention relates to an improved real-time scanning fluorescence electrophoresis apparatus for the electrophoretic analysis of fluorescently-labeled polynucleotide fragments. The apparatus is characterized by having an electrophoresis chamber containing an electrophoretic separation medium capable of accommodating multiple electrophoresis lanes arranged in a planar array, a fluorescence detector mounted on a translatable stage, a light source for exciting fluorescent molecules, and a computer for collecting data consisting of time, location, fluorescence wavelength and fluorescent intensity information. The improvements herein disclosed include, (i) using a spectral-array detector for detecting the emission light from the fluorescently-labeled polynucleotide fragments including the simultaneous detection of multiple fluorescent labels, and, (ii) a temperature control means to control the temperature of the electrophoretic separation medium during electrophoresis.

14 Claims, 5 Drawing Sheets

REAL-TIME SCANNING FLUORESCENCE ELECTROPHORESIS APPARATUS FOR THE ANALYSIS OF POLYNUCLEOTIDE FRAGMENTS

FIELD OF THE INVENTION

This invention relates to improved apparatus for performing electrophoresis, and more particularly to an improved real-time scanning fluorescence electrophoresis apparatus for polynucleotide fragment analysis.

BACKGROUND OF THE INVENTION

Electrophoretic polynucleotide fragment analysis methods are used to characterize mixtures of polynucleotide fragments based on their migration velocity through a polymer network under the influence of an electric field, i.e. their electrophoretic mobility, in combination with single or multi-color fluorescence detection. Typically these methods are applied subsequent to amplification of the target polynucleotide using a method such as PCR, e.g. Mullis, U.S. Pat. No. 4,683,202. Examples of such methods include polynucleotide sequencing, e.g. Trainor, Anal. Chem., 62:418–426 (1990), restriction fragment length polymorphisim (RFLP) analysis, e.g. Watkins, Biotechniques, 6:310–319 (1988), and variable number of tandem repeat (VNTR) or microsatellite analysis, e.g. Ziegle et al., Genomics, 14:1026–1031. Each of these methods can provide valuable genetic information about the target polynucleotide.

Current electrophoretic polynucleotide fragment analysis systems are characterized by multiple electrophoresis lanes arranged in a planar array, e.g. a multi-lane slab gel, in combination with a real-time-scanning fluorescence detector, e.g. Hunkapiller et al., U.S. Pat. No. 4,811,218. Multiple lanes are used to increase the overall throughput of the analyzer. In order to collect data during the electrophoresis from multiple lanes, the optical detector system is scanned across the width of the electrophoresis chamber perpendicular to the direction of migration of the labeled polynucleotides. Preferably, multi-color fluorescence detection is used to increase the information density per lane, e.g. for DNA sequencing, four label colors are used, one color for each base. A light source, e.g. a laser, excites the fluorescent labels attached to the polynucleotide fragments, and multiple emission filters discriminate between labels having different spectral properties. In addition, a computer is used to collect data consisting of time, lane number, and fluorescence emission wavelength information, and transform it into useful information, e.g. DNA sequence.

A significant limitation on the speed and resolution of current polynucleotide fragment analysis systems is the ability to dissipate the Joule heat that is generated as a result of the electric current passing through the electrophoresis medium. Because of problems caused by Joule heating, current systems are limited to low, e.g. 25 V/cm, electrical fields, resulting in long analysis times, e.g. 8 hrs. Joule heating and the resulting temperature gradient across the gel can negatively impact the quality of the separation in two ways. First, because heat is generated throughout the electrophoresis medium but only dissipated at its' outside surfaces, a parabolic temperature profile is establish across the depth of the channel. Since electrophoretic velocity is a strong function of temperature, approximately 2% per °C., this temperature profile leads to a parabolic velocity profile for the migrating analytes. This spatial dependence of velocity causes a broadening of the migrating zones, leading to reduced separation performance. The extent of the temperature profile can be reduced by making the electrophoresis channel thinner, e.g. Brumley et al., Nucleic Acids Research, 19:4121–4126 (1991); Stegemann et al., Methods in Molecular and Cellular Biology, 2:182–184 (1991). Therefore, an automated system which incorporates thin electrophoresis channels would be desirable.

Second, if the average temperature of the electrophoresis medium becomes too high, the structural integrity of the medium can be compromised. In the case of polymer gel media, e.g. crosslinked polyacrylamide gels, the elevated temperature can lead to complete destruction of the gel. The average temperature of the electrophoresis medium can be controlled by increasing the rate of heat transfer from the electrophoresis channel to the surrounding environment. Therefore, a system which more efficiently transfers the Joule heat generated as a result of the electrophoresis to the surrounding environment would be desirable.

A further limitation on the speed and resolution of electrophoretic separations is the rate at which the detector can acquire data from fast moving analyte bands. The most desirable form of detection for polynucleotide fragment analysis would be simultaneous multi-color detection. However, current approaches, i.e. an indexable filter wheel in combination with a photomultiplier tube (PMT) detector, are not ideal because the filter wheel must be indexed rapidly enough to observe each color before it moves out of the detector region. This is problematic due to the high electrophoretic velocity of the polynucleotide fragments in high-speed systems. If a sufficient number of data points are not collected for each analyte band, e.g. 10 points per band, the ability to discriminate between adjacent bands is lost. One way to increase the rate of data acquisition for a multi-color system is to collect signals from all the colors simultaneously rather than serially. Therefore, a detection system which acquires all colors simultaneously would be desirable.

In light of the above, what was needed was an improved electrophoresis apparatus capable of accommodating high electric fields through enhanced heat dissipation characteristics and detector performance.

SUMMARY OF THE INVENTION

The present invention is directed to improvements to an apparatus for electrophoretic polynucleotide analysis, said improvements leading to increased throughput of the system. The improvements include (i) incorporating a spectral-array detector to increase the rate of data acquisition, and (ii) incorporating an improved means to control the temperature of the electrophoresis medium. The analyzer system of the present invention is comprised of, in combination.

An improved real-time scanning fluorescence electrophoresis apparatus for the electrophoretic analysis of fluorescently-labeled polynucleotide fragments of the type having an electrophoresis chamber containing an electrophoretic separation medium capable of accommodating multiple electrophoresis lanes arranged in a planar array, a fluorescence detector mounted on a translatable stage, a light source for exciting fluorescent molecules, and a computer for collecting data consisting of time, location, fluorescence wavelength and fluorescent intensity information wherein the improvement comprises:

(a) a spectral-array detector for detecting the emission light from said fluorescently-labeled polynucleotide fragments including the simultaneous detection of multiple fluorescent labels, (b) a temperature control means to control the temperature of the electrophoretic separation medium during electrophoresis.

DEFINITIONS

The term "polynucleotide" as used herein refers to linear polymers of natural or modified nucleoside monomers, including double and single stranded deoxyribonucleosides, ribonucleosides, α-anomeric forms thereof, and the like. Usually the nucleoside monomers are linked by phosphodiester bonds or analogs thereof to form polynucleotides ranging in size from a few monomeric units, e.g. 8–40, to several thousands of monomeric units. Whenever a polynucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilothioate, phosphoranilidate, phosphoramidate, and the like.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Arealogs (John Wiley, New York, 1980).

As used herein, the term "electrophoretic separation medium" refers to a material through which the polynucleotides are electrophoresed and which imparts a size-dependent electrophoretic velocity to the polynucleotides. Typically, such material is a porous network formed by linear or branched polymer molecules, or the like, e.g. crosslinked polyacrylamide.

As used herein, the term "electrophoresis chamber" refers to the container in which the electrophorertic separation is contained. Typically, this container is formed by two rectangular glass plates which are separated by thin polymer sheets, spacers, located between the plates at the edge regions of the plates. This is traditionally referred to as slab electrophoresis. When the electrophoretic separation medium is a rigid crosslinked gel, this format is referred to as slab gel electrophoresis.

DESCRIPTION OF THE PREFERRED EMBODIMENTS

Figure 1:
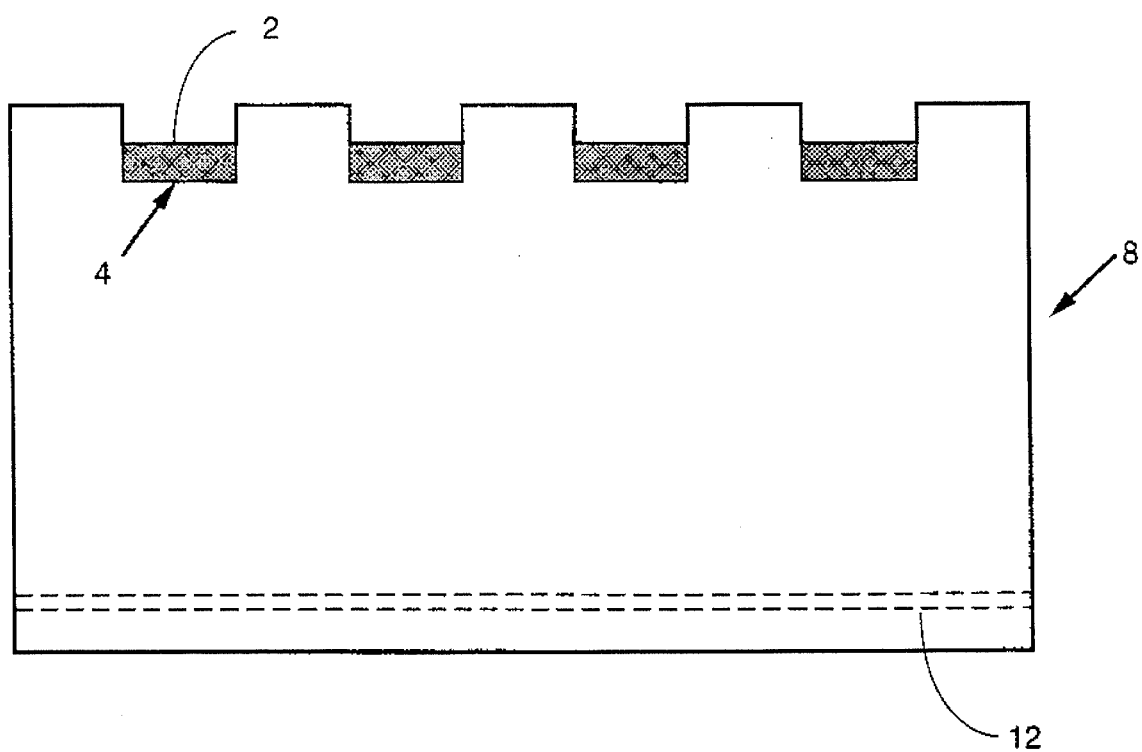
FIG. 1 shows an electrophoresis gel including sample loaded thereon.

FIG. 1 shows polynucleotide fragment samples (2) which have been labeled with one of several fluorophores loaded into loading wells (4) of vertically oriented slab gel (8), said gel mounted in the analyzer of the present invention.. The fragments are electrophoresed through gel (8) where they are separated based on their relative size. Following separation, the fragments pass through laser excitation and detection region (12) where the fluorescently labeled polynucleotide fragments are detected. The fluorophores emit light at a specific wavelength based upon the particular dye used, thereby facilitating the identification of each fragment.

After the polynucleotide fragments have been separated, they are detected by a simultaneous multi-color detection means. An important feature of the polynucleotide analyzer of the present invention is the "spectral-array fluorescence detector". As used herein, the term "spectral-array fluorescence detector" refers to a detector which employs (i) a means to spectrally separate the fluorescence emission light, such as a diffraction grating, or a prism, or the like, (ii) an array of detector elements sensitive to light radiation, such as a diode array, a charged coupled device (CCD) system, an array of photomultiplier tubes, or the like, (iii) an excitation light source, such as an incandescent bulb, an arc lamp, a laser, a laser diode, or the like, and (iv) associated optics capable of directing and conditioning both the excitation and emission light. The output of a spectral-array detector is light intensity as a function of array location, wherein the array location can be directly related to the wavelength of the light falling on that location. One example of such a detector is given by Karger et al., Nucleic Acids Research 19: 4955–4962 (1991).

One preferred method of treating the output of a spectral-array detector is to create a "virtual filter". As used herein, the term "virtual filter" refers to a method of manipulating data from a spectral-array detector such that a plurality of discrete wavelength ranges are sampled, wherein the location and bandwidth of each wavelength range can be dynamically changed using software. The virtual filter can mimic a physical interference or absorbence filter, however it has several important advantages. First, virtual-filters can be programmed to interrogate multiple emission wavelengths simultaneously, making possible the efficient multi-color detection of fast-moving analytes without the need to rapidly index a multiplicity of filters. Second, virtual filters can be programmed to detect a range of emission bandwidths. This is important because for any application, there exists an optimum bandwidth which results in an optimum combination of sensitivity and color discrimination: as the detection band width is made wider, the detector collects more light, thereby increasing sensitivity, however, at the same time, the broader bandwidth decreases the ability to discriminate between closely related colors. Third, virtual filters have essentially perfect transmission curves, i.e. the filter can discriminate between very closely related colors. Forth, the selected wavelength ranges of the virtual filter can be easily adjusted using software to match the characteristics of various excitation light sources and dye sets. Therefore, changing dye chemistries is a simple matter of changing the virtual filter with software, whereas a mechanical modification of the system is required when physical filters are used. Moreover, the selected wavelength ranges and band widths of the virtual filter can be changed dynamically, i.e. during the course of a run, to compensate for any spectral changes in the dye labels which occur during a run.

Figure 2:
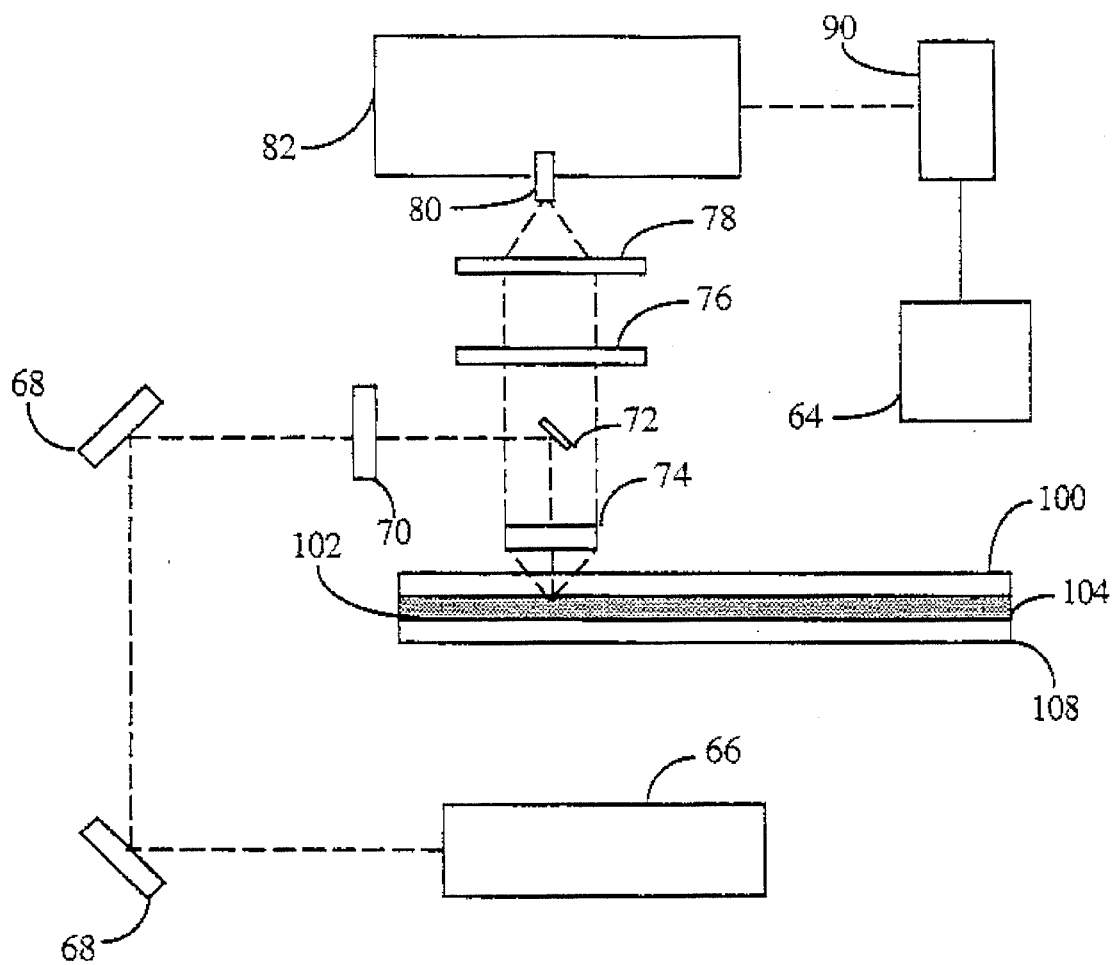
FIG. 2 is a diagram of the illumination, collection and detection optics employed in the invention.

FIG. 2 is a schematic diagram of the light path in a preferred embodiment of the spectral-array detection system of the present invention. Preferably, the analyzer system of the invention uses a laser as a fluorescence excitation light source, e.g. an argon ion laser that emits a 40 mW, 0.67 mm diameter polarized light beam having intensity maxima at wavelengths of 488 and 514 nm. Light from laser (66) is reflected off of adjustably-mounted turning mirrors (68) which direct the laser light to the desired location. Telescope lenses (70) then reduce the beam diameter to approximately 100 μm, and bending mirror (72) directs the light into electrophoresis medium (104) at right angles.

Light emitted from the laser-excited fluorescent label is collected by aspheric collection lens (74) which collimates the light in the direction of the detector. The emitted light then passes around bending mirror (72) and through laser rejection filter (76), thereby reducing the level of scattered laser light entering the detector. Because the excitation laser light passes through the center of aspheric collection lens (74), a certain amount of laser light will be reflected directly back from the lens surface in the direction of the detector, causing unwanted background signal. Bending mirror (72), which is mounted in the center of laser rejection filter (76), acts to deflect this reflected light away from the collection path thus reducing the amount of reflected light entering the detector. The collected emission light then passes through plano-convex lens (78) which focuses the emission light at slit (80) mounted on the entrance to spectrograph (82). (Spectrograph (82) utilizes a 405 g/mm, 450 nm blaze grating with a dispersion of 17 nm/mm.) After passing through spectrograph (82), the light then falls onto CCD (90). The output signal from CCD (90) is transmitted to electronic computer (64) for subsequent data analysis and presentation.

To further increase the emission light signal and decrease background light scatter, a nonconductive mirror coating is applied to inside surface (102) of front gel plate (108). This surface reflects emission light back to the collection lenses rather than allowing it to be lost to the surroundings through the front gel plate. In addition, when the primary laser light strikes this mirrored surface it is reflected back through the gel, thereby exciting additional fluorophores resulting in more emission light. Furthermore, this mirrored surface decreases unwanted background light generated by the fluorescence of the front glass plate itself.

In order to interrogate all of the electrophoresis lanes on a real-time basis, the optical system described above, less turning mirrors (68) and computer (90), is scanned across the width of the electrophoresis chamber.

Figure 3:
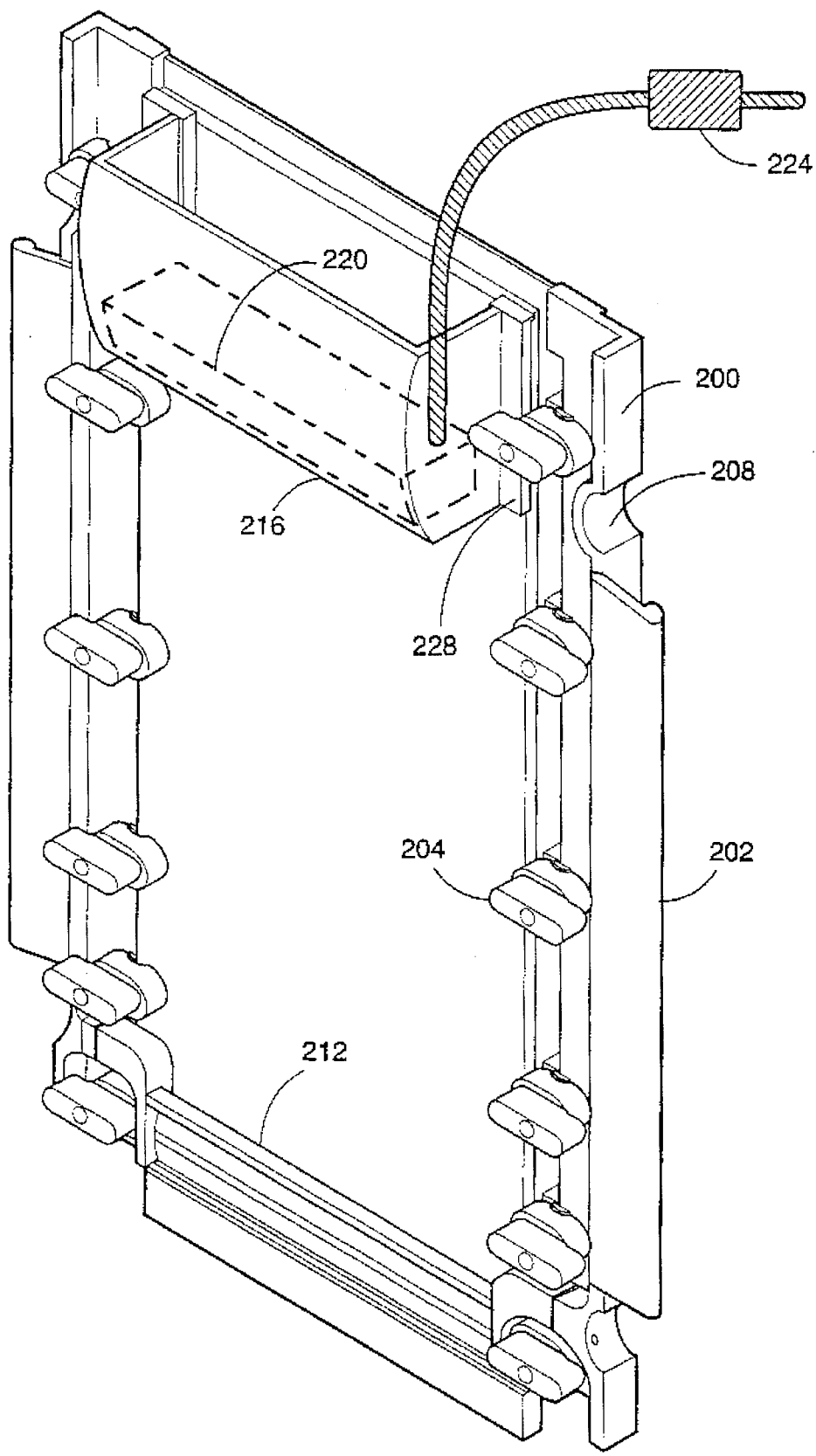
FIG. 3 shows a plate holder of the invention.

Another important feature of the present invention is the novel means used to mount the electrophoresis chamber onto the analyzer. Preferably, the electrophoresis chamber is formed by two glass plates separated by two spacers located at the left and right edges of the plates. The glass plates are mounted into a plate holder which acts to support and secure the glass plates along with an upper buffer reservoir in a convenient manner. See FIG. 3. The plate holder consists of rectangular frame (200) onto which is attached plurality of twist clamps (204). (Note that only one twist clamp is indicated in FIG. 3, as (84), in order to retain the clarity of the drawing.) When twist clamps (84) are in the horizontal orientation, they serve to secure the glass plates in the holder, and, when twist clamps (84) are in a vertical orientation, they allow the glass plates to be conveniently inserted or removed from the plate holder. The rectangular frame includes two locational registration notches (208) to insure the proper positioning of the plate holder in the analyzer. Beam-stop (212) is positioned so as to protect the user from direct exposure to the excitation laser light. The frame also includes two handles (202) to facilitate transportation of the plate holder assembly. The plate holder provides a means for detachably mounting upper buffer reservoir (216). A protrusion (228) on each side of upper buffer reservoir (216) is positioned such that when the uppermost twist clamps are in the horizontal position, the upper buffer reservoir (216) is forced against the front glass plate, thereby creating a liquid-tight seal between the upper buffer chamber and the front glass plate. Upper buffer reservoir (216) contains electrode (220) and electrical cable (224) for connecting electrode (220) to an electrophoresis power supply. The plate holder is designed to secure glass plates of varying lengths. For applications requiring less separation and/or a shorter analysis time, a shorter length would be used, and for applications requiring more separation and for which longer analysis times can be tolerated, a longer length would be used.

Figure 4A:
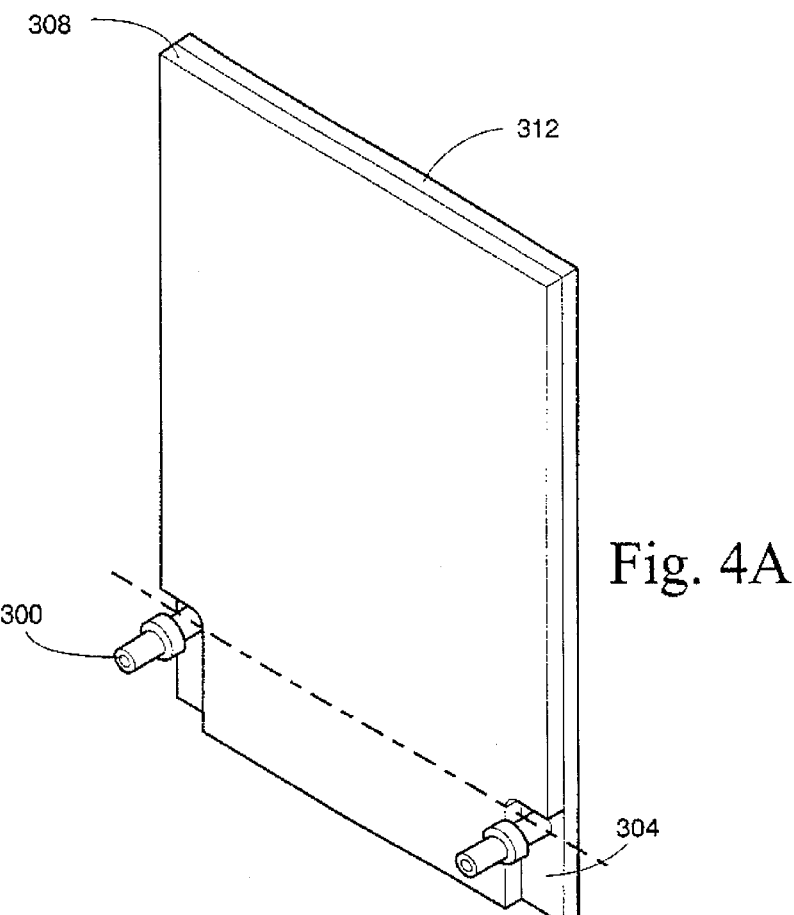
FIG. 4A, 4B, and 4C show a plate locating mechanism of the invention.
Figure 4B:
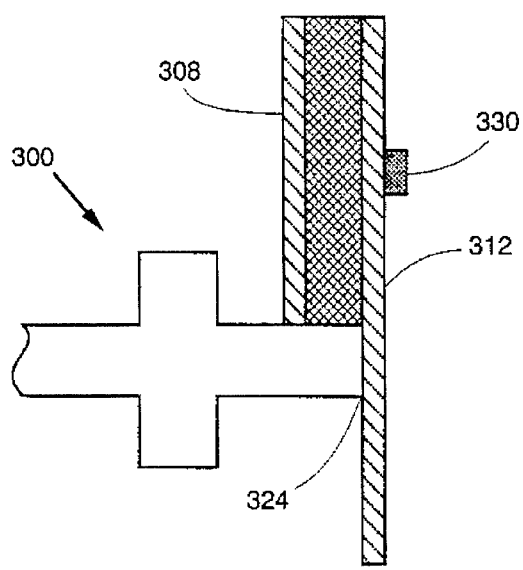
Figure 4C:
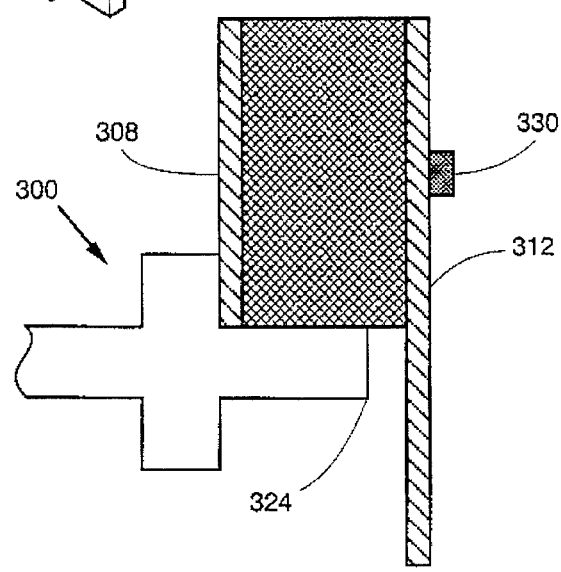

A further important aspect of the present invention is the plate locating mechanism. In order to efficiently collect the fluorescence emission light, the detection region of the electrophoresis chamber must be properly positioned with respect to the collection optics. Specifically, the detection region must be aligned such that the focal point of the collection optics is located within the separation medium, and not in the wall of the electrophoresis chamber. The plate locating mechanism insures that this positioning is reproducibly achieved. The mechanism will be described with reference to FIG. 4. When a thin electrophoresis chamber is being used, i.e. less than 0.2 mm, preadjusted locating pins (300) fit through notches (304) in back glass plate (308) and push front glass plate (312) against front tip (324) of locating pins (300). When a thick electrophoresis chamber is being used, i.e. greater than 0.2 mm, step-portion (320) of locating pins (300) is forced against back glass plate (312). Locating pins (300) are preadjusted such that the interior of the electrophoresis chamber is at the focal point of the collection optics. Glass plates (308 and 312) are forced against locating pins (300) by twist clamps (330).

Figure 5:
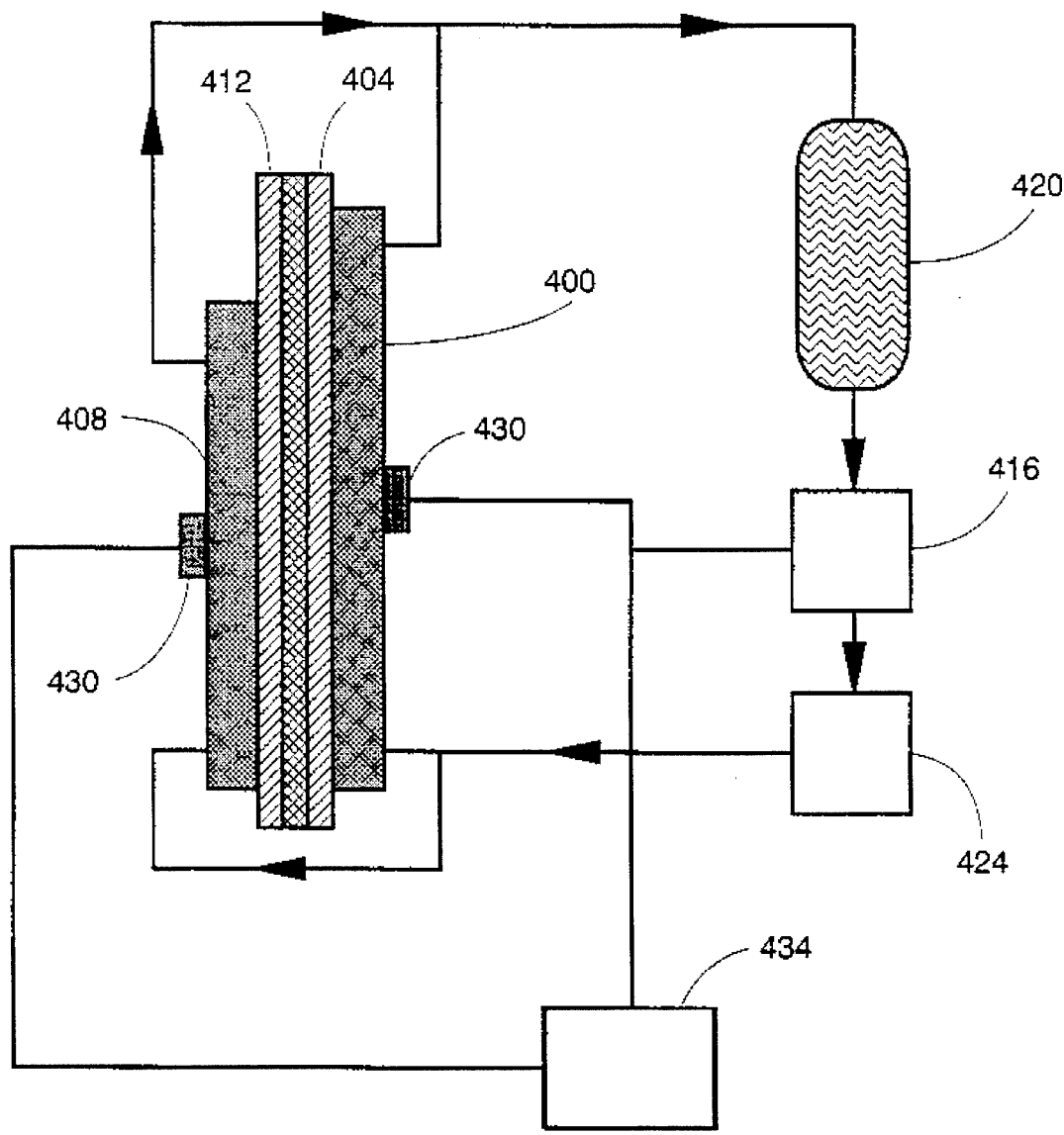
FIG. 5 is a diagram of a thermal control system used in the invention.

While increasing the electric field across the electrophoresis chamber increases the speed of the electrophoretic separation, it also leads to increased Joule heat generated within the electrophoresis medium, which in turn can lead to destruction of the electrophoresis medium. To remove the heat generated by running "fast" electrophoresis, a temperature control mechanism (FIG. 5) has been developed. The temperature control mechanism includes a back heat transfer plate (400) against which back glass plate (404) is mounted to the instrument. Preferably, heat transfer plate (400) is made from coated aluminum. The coating acts as an electrical insulator to inhibit arcing between back glass plate (404) and the rest of the instrument. Within back cooling plate (400) are channels through which a flowable heat transfer medium can be circulated. Front heat transfer plate (408), also containing channels capable of being filled with a flowable heat transfer medium, is contacted with front glass plate (412). Pump (416) circulates the flowable heat transfer medium from reservoir (420) through front and back heat transfer plates (400 and 408). Heat is removed from the circulating flowable heat transfer medium by passing it through heat exchanger (424), thereby cooling the flowable heat transfer medium to ambient temperature. If superambient heating or subambient cooling of the gels is desired for a specific application, the flowable heat transfer medium passes through a heater or cooler (not shown) before flowing through the heat transfer plates. Active temperature control of the gel is effected by means of temperature sensors (430) mounted to the heat transfer plates in combination with computer (434) which regulates the temperature of the plates by controlling the flow rate of the flowable heat transfer medium through the heat transfer plates.

Although the invention has been illustrated by the foregoing description it is not to be construed as being limited to the materials employed therein but rather the invention is directed to the generic area as hereinbefore disclosed. Various modifications and embodiments thereof can be made without departing from the spirit or scope thereof.

We claim:

1. An improved real-time scanning fluorescence electrophoresis apparatus for the electrophoretic analysis of fluorescently-labeled polynucleotide fragments comprising:

an electrophoresis chamber including a front gel plate for containing an electrophoresis separation medium and defining a plurality of electrophoresis lanes;

a laser light source for creating a beam of laser light;

a bending mirror for directing the laser light into the electrophoresis chamber at right angles to the front gel plate;

a spectral-array fluorescence detector for detecting emission light from said fluorescently-labeled polynucleotide fragments including simultaneous detection of multiple fluorescent labels:

a translatable stage for mounting the spectral-array fluorescence detector and the bending mirror thereon for translating the bending mirror and the spectral-array fluorescence detector with respect to the electrophoresis chamber for scanning the beam of laser light and the spectral-array fluorescence detector across the electrophoresis chamber in a direction parallel to the front gel plate and normal to the direction of migration of the polynucleotide fragments; and a temperature control means to control the temperature of the electrophoretic separation medium during electrophoresis.

2. The apparatus of claim 1 wherein an output of the spectral-array detector is processed so as to effect a virtual filter, such filter effecting the sampling of a plurality of discrete wavelength ranges.

3. The apparatus of claim 2 wherein the wavelength ranges of said virtual filter are 540, 560, 580, and 610 nm, each 10 nm wide.

4. The apparatus of claim 2 wherein the wavelength ranges of said virtual filter are 530, 545, 560, 580 nm, each 10 nm wide.

5. The apparatus of claim 1 wherein the spectral-array detector comprises:

(a) a diffraction grating to separate the emission light, (b) a CCD array to detect a location and an intensity of the separated emission light, (c) an optical arrangement to direct and condition the beam of laser light and the emission light in order to minimize scattered laser light reaching the detector.

6. The spectral-array detector of claim 5 having an optical arrangement comprising:

turning mirrors which direct the laser light to a desired location, telescopic lenses which focus the laser light to a position within the electrophoresis chamber, a bending mirror that directs the laser light at right angles to the electrophoresis chamber, an aspheric collection lens that collimates the emission light, a set of laser rejection filters that reduce extraneous laser light entering the detector, and, a plano-convex lens which focuses the emission light at a desired location.

7. The apparatus of claim 1 wherein the temperature control means comprises thermally controlled front and back heat transfer plates which are in contact with a front and back face of the electrophoresis chamber.

8. The apparatus of claim 7 wherein the front and back heat transfer plates are made from coated aluminum wherein the coating acts to electrically insulate the heat transfer plates from an electrophoresis voltage.

9. The apparatus of claim 7 wherein the temperature control means comprises:

(a) a front heat transfer plate placed in contact with a front face of the electrophoresis chamber, wherein flow channels are formed within the front heat transfer plate including inlet and outlet ports, (b) a back heat transfer plate placed in contact with a back face of the electrophoresis chamber, wherein flow channels are formed within the back heat transfer plate including inlet and outlet ports, (c) a flowable heat transfer medium which is circulated through the flow channels in the front and back heat transfer plates, (d) a pump to circulate the flowable heat transfer medium, (e) a heat exchanger in which the flowable heat transfer medium can exchange heat with an ambient atmosphere, (f) a computer for controlling a temperature of the heat transfer plates by controlling the flow of the circulating heat transfer medium, (g) a temperature sensor in contact with the front and back heat transfer plates and electrically connected to the computer to relay temperature information to the computer.

10. The apparatus of claim 9 wherein said heat exchanger is replaced by a cooler wherein the cooler cools the flowable heat transfer medium below the temperature of the ambient atmosphere.

11. The apparatus of claim 9 wherein said heat exchanger is replaced by a heater wherein the heater heats the flowable heat transfer medium above the temperature of the ambient atmosphere.

12. The apparatus of claim 1 wherein the electrophoresis chamber comprises:

(a) a front plate and a back plate, where the back plate is defined as a plate through which the laser light enters the electrophoresis chamber, (b) two spacers which serve to maintain a uniform separation between the glass plates, spaced so as to provide a chamber thickness of from about 0.1 to about 1.0 mm, (c) a plate holder which can accommodate glass plates of varying lengths and which acts to support and secure said electrophoretic separation medium and wherein said plates are held firmly in place within the plate holder by clamps which keep the edges of the plates sealed to prevent said separation medium from leaking.

13. The apparatus of claim 12 further comprising a plate locating mechanism which optimally positions a detection region of the electrophoresis chamber with respect to a detection optics.

14. The apparatus of claim 12 further comprising a mirror coating applied to an inside-facing surface of the front plate so that the excitation laser light, after passing through the back plate and the electrophoresis chamber, strikes the mirror coating and is reflected back through the electrophoresis chamber, thereby exciting additional fluorophores whose light is then collected, resulting in an increased emitted light signal.

* * * * *

UNITED STATES PATENT AND TRADEMARK OFFICE
CERTIFICATE OF CORRECTION

PATENT NO. : 5,543,026
DATED : August 6, 1996
INVENTOR(S) : Louis B. Hoff, Eric W. Lachenmeier, Yefim M. Raysberg, Eric S. Nordman It is certified that error appears in the above-indentified patent and that said Letters Patent is hereby corrected as shown below:

Column 5, lines 53, 54, and 56, delete "(84)" and insert --(204)--.

Column 6, line 32, delete "(308 and 312)" and insert --(308 or 312)--.

Signed and Sealed this

Twenty-sixth Day of November 1996

Attest:

BRUCE LEHMAN

Attesting Officer    Commissioner of Patents and Trademarks